United States Patent [19]

Gammill

[11] Patent Number: 4,463,185

[45] Date of Patent: Jul. 31, 1984

[54] 1-(6-HYDROXY-4- OR -7-METHOXY-5-BENZOFURANYL)-4-SUBSTITUTED-1,3-BUTANEDIONES

[75] Inventor: Ronald B. Gammill, Portage, Mich.

[73] Assignee: The Upjohn Company, Kalamazoo, Mich.

[21] Appl. No.: 403,948

[22] Filed: Jul. 30, 1982

Related U.S. Application Data

[60] Continuation-in-part of Ser. No. 201,932, Oct. 29, 1980, Pat. No. 4,367,341, which is a division of Ser. No. 116,322, Jan. 28, 1980, Pat. No. 4,284,569, which is a continuation-in-part of Ser. No. 11,816, Feb. 13, 1979, abandoned.

[51] Int. Cl.$^3$ .................. C07D 307/86; C07D 307/78
[52] U.S. Cl. .................................... 549/471; 544/153; 544/376; 546/196
[58] Field of Search ........................................ 549/471

[56] References Cited

U.S. PATENT DOCUMENTS 2,680,119  6/1954  Robertson et al. ............... 260/345.2
4,284,569  8/1981  Gammill ........................ 260/345.2

OTHER PUBLICATIONS

R. Aneja, et al., A New Synthesis of Khellin, J. Sci. Industr. Res., 17B:382–383 (1958).
R. Aneja, et al., Neue Synthesen von Khellin, Chem. Ber., 93:297–303 (1960).
R. A. Baxter, et al., Furochromones. Part I. The Synthesis of Khellin, J. Chem. Soc., pp. S30–S33 (1949).
J. R. Clarke, et al., Furano-compounds. Part IX., The Synthesis of Kellin and Related Compounds, J. Chem. Soc., pp. 302–307 (1949).
O. Dann, et al., Eine Neue Synthese von Khellin und Anderen Furo–2–Methyl–Chromonen, Ann. Chem. 605:146–157 (1957).
O. Dann, et al., Synthese von 2–Methyl–5.8–dihydroxy-furano–[3'.2':6.7]–Chromon und von Khellin, Chem. Berg., 93:2829–2833 (1960).
T. S. Gardner, et al., The Synthesis of Khellin Derivatives, J. Org. Chem., 15:841–849 (1950).
T. A. Geissman, et al., Chromones. III., A Total Synthesis of Khellin, J. Amer. Chem. Soc., 73:1280–1284 (1951).
V. V. S. Murti, et al., A Synthesis of Kellin, J. Sci. Ind. Res. (India) 8B:112–113 (1949).
V. V. S. Murti, et al., Nuclear Oxidation in Flavones and Related Compounds Part XXIII., Proc. of the Indian Acad. of Sci., 30A:107–113 (1949).
C. Musante, Prodotti di scissione alcalina della Khellina e loro derivati e trasformazione del sistema del furo--cromone in quello del furo–benzo–isossazolo, Gazz. Chim. Ital., 88:910–929 (1958).
A. Mustafa, Furopyrans and Furopyrones, Chapter III, Furochromones, John Wiley and Sons, Inc., New York, pp. 102–159 (1967).
A. Mustafa, Benzofurans, John Wiley and Sons, 1974.
L. R. Rowe, et al., Furanobenzopyrones: Part VII, Indian J. Chem., 5:105–106 (1967).
A. Schonberg, et al., Khellin from Visnagin, J. Amer. Chem. Soc., 73:2960–2961 (1951).
E. Spath et al., Die Konstitution des Kellins, Chem. Ber., 71:106–113 (1938).

*Primary Examiner*—Henry R. Jiles
*Assistant Examiner*—Bernard Dentz
*Attorney, Agent, or Firm*—Lawrence T. Welch; Robert A. Armitage

[57] ABSTRACT

The present invention provides novel 1-(6-hydroxy-4- or 7-methoxy or 4,7-dimethoxy-5-benzofuranyl)-4-substituted-1,3-butanediones which are useful as intermediates in the synthesis of khellin and related anti-atherosclerotic furochromones.

2 Claims, No Drawings

1-(6-HYDROXY-4- OR -7-METHOXY-5-BENZOFURANYL)-4-SUBSTITUTED-1,3-BUTANEDIONES

DESCRIPTION

CROSS REFERENCE TO RELATED APPLICATIONS

This application is a continuation-in-part of Ser. No. 201,932, filed Oct. 29, 1980, now U.S. Pat. No. 4,367,341 which is a division of Ser. No. 116,322, filed Jan. 28, 1980, now U.S. Pat. No. 4,284,569 which is a continuation-in-part of application Ser. No. 011,816, filed Feb. 13, 1979, now abandoned.

BACKGROUND OF THE INVENTION

The present invention relates to intermediates useful in the synthesis of novel furochromones which are khellin analogs and useful for anti-atherosclerotic purposes. Khellin is 7-methyl-4,9-dimethoxyfurochromone. Most particularly, the present invention relates to 1-(6-hydroxy-4- or 7-methoxy- or 4,7-dimethoxy-5-benzofuranyl)-4-substituted-1,3-butanediones, the preparation and use as intermediates for pharmaceuticals is described in U.S. Pat. No. 4,284,569 incorporated here by reference.

For example, 7-methylthiomethyl-4,9-dimethoxyfurochromone is described in U.S. Pat. No. 4,284,569 as such a useful antiatherosclerotic substance.

PRIOR ART

Methods for the total synthesis of khellin are known. For example, pyrogallol has been employed as a starting material for the synthesis of furochromones such as khellin. See Clarke, J. R., et al., J. Chem. Soc., 302 (1949), Baxter, R. A., et al., J. Chem. Soc., S30 (1949), Schonberg, A., et al., J. Am. Chem. Soc., 73:2960 (1951), Murti, V. V. S., et al., Proc. of the Indian Acad. of Sci., 30A:107 (1949), and Geissman, T. A., et al., J. Am. Chem. Soc., 73:1280 (1951). Also descriptive of the synthesis of khellin are Spath, E., et al., Chem. Ber., 71:106 (1938), Dann, O., et al., Chem. Ber., 93:2829 (1960), Dann. O., et al., Ann. Chem., 605:146 (1957), and Murti, V. V. S., et al., J. Sci. Ind. Res. (India), 8B:112 (1949). See also U.S. Pat. No. 2,680,119 describing the synthesis of khellin and related compounds.

Other references describing the synthesis of intermediates useful in the preparation of khellin for analogs include: Aneja, R., et al., Chem. Ber., 93:297 (1960), Aneja, R., et al., J. Sci. Ind. Res. (India), 17B:382 (1958), Gardner, T. S., et al., J. Org. Chem., 15:841 (1950), and Rowe, L. R., et al., Indian J. Chem., 5:105 (1967).

Accordingly, the references cited above describe the preparation of 1-(6-hydroxy-4,7-dimethoxy-5-benzofuranyl)-ethanone. Also known is the related compound 6-hydroxy-4,7-dimethoxy-5-benzofurancarboxylic acid, methyl ester, described by Musante, C., Gazz. Chim. Ital., 88:910 (1958).

Most typically, however, the total synthesis of furochromones from benzofurans has been accomplished by utilizing a substituted benzene ring from which to synthesize the fused benzofuran ring system. See Mustafa, A., "Benzofurans," John Wiley and Sons, 1974, and Mustafa, A., "Furopyrans and Furopyrones, Chapter 3: Furochromones," John Wiley and Sons, New York, N.Y., 1967.

The use of pyrogallol in the synthesis of khellin intermediates is known. For example, the transformation of pyrogallol to the khellin intermediate 1-(2,3-dihydro-6,7-dihydroxy-5-benzofuranyl) ethanone is known. The parahydroxylation of this intermediate is also known. See Row, L. R., et al., Indian J. Chem., 5:105 (1967) describing this transformation and the subsequent dimethylation to yield known khellin intermediates.

SUMMARY OF THE INVENTION

The present invention particularly provides a compound of the formula

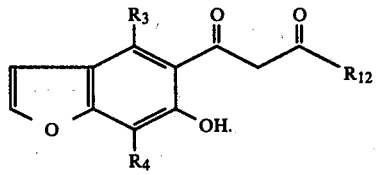

XXIII wherein one of $R_3$ or $R_4$ is methoxy and the other is methoxy or hydrogen;

wherein $R_{12}$ is:

(a) alkyl of one to 8 carbon atoms, inclusive;
(b) alkoxymethyl of 2 to 8 carbon atoms, inclusive;
(c) alkylthioalkyl of 2 to 8 carbon atoms, inclusive;
(d) trifluoromethyl;
(e) phenoxymethyl;
(f) phenylthiomethyl;
(g) phenoxymethyl or phenylthiomethyl substituted by chloro, fluoro, trifluoromethyl, alkyl of one to 3 carbon atoms or alkoxy of one to 3 carbon atoms; or
(h) cycloalkyl of 3 to 10 carbon atoms, inclusive;
(i) $-CH_2-S-R_{10}$, $-CH_2-SO-R_{10}$, or $-CH_2-SO_2-R_{10}$, wherein $R_{10}$ is alkyl of one to 5 carbon atoms, inclusive; or
(j) $-CH_2NR_8R_9$, wherein $R_8$ and $R_9$ are hydrogen, alkyl of one to 12 carbon atoms, inclusive, or aryl of 6 to 12 carbon atoms, inclusive, being the same or different, or wherein $R_8$ and $R_9$, taken together with N, form a saturated or unsaturated heterocyclic amine ring consisting of from 2 to 7 carbon atoms, inclusive, and zero, one, or 2 additional hetero atoms, with the proviso that said heterocyclic amine ring contains 4 to 8 atoms in the ring, said additional hetero atoms being selected from the group consisting of oxygen, nitrogen, and sulfur, said heterocyclic amine ring being optionally substituted by alkyl of one to 4 carbon atoms, inclusive, alkylthiomethyl or alkoxymethyl of 2 to 8 carbon atoms, inclusive, hydroxyalkyl of one to 4 carbon atoms, inclusive, or phenyl, with the proviso that $R_{12}$ is $-CH_2NR_8R_9$ only when $R_4$ is methoxy.

These compounds are useful as intermediates for the preparation of khellin or other anti-atherosclerotic agents as described in U.S. Pat. No. 4,284,569.

DESCRIPTION OF THE PREFERRED EMBODIMENTS

The present invention is more completely understood by the operation of the following examples:

EXAMPLE 1

1-(6-Hydroxy-4,7-dimethoxy-5-benzofuranyl)-4-methylthio)-1,3-butanedione

Sodium methoxide is added to a flame-dried 2 l, 3-neck round-bottomed flask under a blanket of nitrogen. The flask is equipped with a mechanical stirrer, reflux condenser, and addition funnel (500 ml). Toluene (400 ml) is added to the sodium methoxide, 6-Hydroxy-4,7-methoxy-5-benzofuranyl methyl ketone (Example 1, U.S. Pat. No. 4,284,569, 100 g) and ethyl 2-(methylthio) acetate (85.2 g) are dissolved in toluene (400 ml) and briefly heated to obtain a homogeneous solution. The resulting homogeneous solution is then transferred to the addition funnel. This solution is then added to the sodium methoxide in toluene in a steady stream over 5 min. The addition funnel is then rinsed with toluene (15 ml) and replaced with a glass stopper. The reaction is then heated at reflux for 4 hr and thereafter cooled to 0° C. in an ice bath and transferred to a 4 l flask and diluted with 2 l of 1 normal aqueous hydrochloric acid. This mixture is then vigorously stirred and the toluene layer separated in a separatory funnel. The aqueous layer is then extracted with an additional 500 ml of toluene and the total toluene solution is dried over sodium sulphate (200 g) and the toluene removed under reduced pressure. The resulting dark red oil is then diluted with about 250 ml of toluene and transferred to a 2 l flask. The solution is then heated (with stirring). Skellysolve B has been added until the solution becomes cloudy. The resulting material is then placed in a freezer. After 20 hr, the resulting solid is collected on a filter to yield 117 g of title product. Recrystallization from hot toluene as described above then yields 105.3 g of pure title product.

EXAMPLE 2

7-methylthiomethyl-4,9-dimethoxy furochromone

The title product of Example 1 (5 g) is dissolved in 150 ml of methylene chloride. With stirring florosil (50 g) is added and the resulting mixture is stirred for 30 min. The florosil is then collected on a filter and washed with dichloromethane until the starting material can no longer be detected. Dry hydrochloric acid is then bubbled into the organic solution and that solution is stirred at ambient temperature for 30 min. At this point the solution is orange in color. A volume of water (750 ml) is added to the solution and the resulting mixture is stirred vigorously until the color disappears, about 2 min. The organic layer is then separated and dried over sodium sulphate and concentrated under reduced pressure to yield 3.24 g of title product. Recrystallization from 25 ml of ethyl acetate yields 1.87 g of pure title product, melting point 150°–152° C.

I claim:

1. A compound of the formula

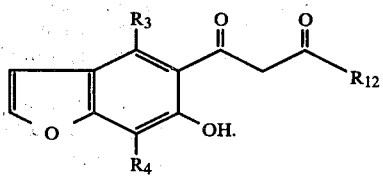

XXIII wherein one of $R_3$ or $R_4$ is methoxy and the other is methoxy or hydrogen;

wherein $R_{12}$ is:

(a) alkylthioalkyl of 2 to 8 carbon atoms, inclusive;
(b) trifluoromethyl;
(c) cycloalkyl of 3 to 10 carbon atoms, inclusive; or
(d) —$CH_2$—SO—$R_{10}$ or —$CH_2$—$SO_2$—$R_{10}$, wherein $R_{10}$ is alkyl of one to 5 carbon atoms, inclusive.

2. 1-(6-Hydroxy-4,7-dimethoxy-5-benzofuranyl)-4-methylthio)-1,3-butanedione, a compound according to claim 1.

* * * * *